United States Patent [19]

Watanabe

[11] Patent Number: 5,641,913
[45] Date of Patent: Jun. 24, 1997

[54] METHOD AND APPARATUS FOR ACCURATE MEASUREMENT OF PULL STRENGTH OF BUMP ELECTRODES ON SEMICONDUCTOR DEVICES

[75] Inventor: Yusuke Watanabe, Obu, Japan

[73] Assignee: Nippondenso Co., Ltd., Kariya, Japan

[21] Appl. No.: 423,358

[22] Filed: Apr. 18, 1995

[30] Foreign Application Priority Data

Oct. 7, 1994 [JP] Japan .................. 6-244316

[51] Int. Cl.$^6$ .................................................. G01N 3/08
[52] U.S. Cl. ......................................... 73/827; 73/831
[58] Field of Search ........................... 73/826, 827, 830, 73/828, 831, 834, 845, 848, 850, 851, 847, 788, 783

[56] References Cited

U.S. PATENT DOCUMENTS

| | | | |
|---|---|---|---|
| 3,213,667 | 10/1965 | Gettys | 73/827 |
| 3,945,248 | 3/1976 | West | 73/88 B |
| 4,213,556 | 7/1980 | Persson et al. | 73/827 |
| 4,282,758 | 8/1981 | Wootten et al. | 73/827 |
| 4,453,414 | 6/1984 | Ronemus et al. | 73/827 |
| 4,745,684 | 5/1988 | Brown . | |
| 5,214,963 | 6/1993 | Widder | 73/827 |
| 5,374,808 | 12/1994 | Coultrip et al. | 73/827 |

FOREIGN PATENT DOCUMENTS 2194844  3/1988  United Kingdom .

*Primary Examiner*—Richard Chilcot
*Assistant Examiner*—Max H. Noori
*Attorney, Agent, or Firm*—Cushman, Darby & Cushman IP Group of Pillsbury Madison & Sutro LLP

[57] ABSTRACT

A tensile strength or pull strength testing of a semiconductor bump electrode is measured without mounting a semiconductor chip on a substrate or the like. A probe to be inserted into a semiconductor bump electrode is heated up to a temperature at which a metal of the bump electrode 21 is fused, and then the probe having been heated up to the temperature to fuse the metal of the bump electrode is inserted into the bump electrode so that the metal of the bump electrode is fused. Further, the fused metal of the bump electrode is cooled down together with the probe to solidify the same. Thereafter, the probe fixed within the bump electrode is pulled vertically relative to the bump electrode until the bump electrode breaks. At the time of breakage of the semiconductor bump electrode, the pull force is detected as the pull strength of the bump electrode.

23 Claims, 3 Drawing Sheets

METHOD AND APPARATUS FOR ACCURATE MEASUREMENT OF PULL STRENGTH OF BUMP ELECTRODES ON SEMICONDUCTOR DEVICES

CROSS REFERENCE TO RELATED APPLICATION

This application is based on and claims priority of Japanese Patent Application No. 6-244316 filed Oct. 7, 1994, the content of which is incorporated herein by reference.

BACKGROUND OF THE INVENTION

1. Field of the Invention

The present invention relates to a method and apparatus for testing bump electrodes of semiconductors and, more particularly, to a method and apparatus for testing pull or tensile strength of the same.

2. Related Art

The high density packaging or mounting of electronic circuit elements has been demanded to reduce manufacturing costs of computers, hybrid integrated circuits (ICs) for automotive electronic devices. The flip chip packaging method using semiconductor bump electrodes (bump electrodes) requires less junction areas than other packaging methods and provides higher junction strength. Therefore, it became more attractive as the high density packaging method. From the trend that products are required to be highly integrated type and have multiple functions in recent years, the ICs must be also highly integrated and, hence, the bump electrodes must be finely formed.

It is known as the pull strength or tensile strength testing of those bump electrodes that, as shown in FIG. 5, after forming bump electrodes 21 of a semiconductor chip 20 on a substrate 40, the semiconductor chip 20 is pulled in its entirety by a pulling jig 30 to test the pull strength of the bump electrodes 21. It is also known as disclosed in JP-A-57-2550 that wire leads are connected to bump electrodes and thereafter pulled to test the pull strength of the bump electrodes.

However, in the method of pulling the semiconductor chip 20 to detect the pull strength of the bump electrodes 21 after forming the bump electrodes 21 of the semiconductor chip 20 on the substrate 40 as shown in FIG. 5, the semiconductor chip 20 is pulled in its entirety for the testing. Since the bump electrodes 21 may have different pull strengths, even in the case that only one of the bump electrodes 21 of the semiconductor chip 20 has low strength, it cannot be determined which one has the low strength. It cannot be measured either how low the strength of such one bump electrode 21 of the low strength is. Further, in the method of pulling the wire leads connected to the bump electrodes, it has a problem that, if an adhesive such as the one in the cyanoacrylate system or the like is used to connect the wire leads and the bump electrodes, breakage is likely to occur at the boundary face between the adhesive and the bump electrodes before the breakage of the bump electrodes. It also has a problem that, if the adhesive in the epoxy system is used, the adhesive takes several days to provide its maximum junction strength and is not practical for the testing in a short period of time.

SUMMARY OF THE INVENTION

The present invention has been achieved in consideration of the above-described drawbacks and has an object to enable testing pull strength or tensile strength of semiconductor bump electrodes without mounting a semiconductor chip on a substrate or the like.

The present invention is based upon a knowledge and finding that the pull strength of each bump electrode can be measured as long as the breakage does not occur at junctions between wire leads and bump electrodes.

According to the first aspect of the present invention, a method for testing a pull strength of a semiconductor bump electrode is provided. In this method, a probe is heated up to a temperature at which a metal of the bump electrode is fused and inserted into the metal of the semiconductor bump electrode to fuse the metal of the bump electrode. The fused metal of the bump electrode is cooled down together with the probe to solidify the same and the probe is pulled to break the solidified bump electrode. The pulling force at the time of pulling operation is measured to test the pull strength of the bump electrode.

Preferably, the probe is first inserted into or pressed to the metal of the semiconductor bump electrode and then heated. Further, the probe solidified in the bump electrode is pulled vertically relative to the bump electrode until the bump electrode breaks and the pull force at the time of breakage of the bump electrode is measured. Still further, the pull force at the time of the breakage of the bump electrode is measured by converting the same into an electric signal by a load cell.

According to a second aspect of the present invention, an apparatus for testing a semiconductor bump electrode is provided. This apparatus includes a probe to be inserted into a semiconductor bump electrode, a heater for heating the probe and a pulling device connecting a load cell and the probe and pulling the probe.

Preferably, the apparatus further includes a load cell for converting a force or weight at the time of the breakage of the bump electrode to an electric signal corresponding thereto. The apparatus may include further a probe moving mechanism for holding the load cell and moving the probe up and down and a jig holding the probe at a tip thereof and connecting the load cell and the probe. Still preferably, a heat insulator is interposed between the heater and the load cell for preventing transfer of heat of the heater to the load cell. Further, the metal of the probe has a good wettability with the metal of the bump electrode and is made of a metal or an alloy selected from copper, silver, platinum, iron alloy and copper alloy. Further, the probe has a tip formed in a pointed, rounded or flat shape.

According to the present invention, the pull strength or tensile strength of each bump electrode can be measured without mounting the semiconductor bump electrodes onto the substrate or the like. Further, the breakage does not occur in an adhesive which, if used at the tip of the probe to connect the bump electrodes and the probe, would otherwise break earlier before the breakage of the bump electrodes. Thus, the pull strength or tensile strength and breakage mode of each bump electrode can be measured accurately. Still further, because the heat insulator is interposed between the load cell and the heater to prevent heat transfer of the heater for heating the probe to the load cell, the load cell does not operate erroneously due to the heat and accurate measurement can be attained. Still further, since the probe uses such metal as having a good wettability relative to the metal of the bump electrodes, fixing between the bump electrodes and the probe becomes remarkably strong advantageously.

DETAILED DESCRIPTION OF THE PREFERRED EMBODIMENT

The present invention will be described in full detail hereinunder with reference to the accompanying drawings.

Figure 1:
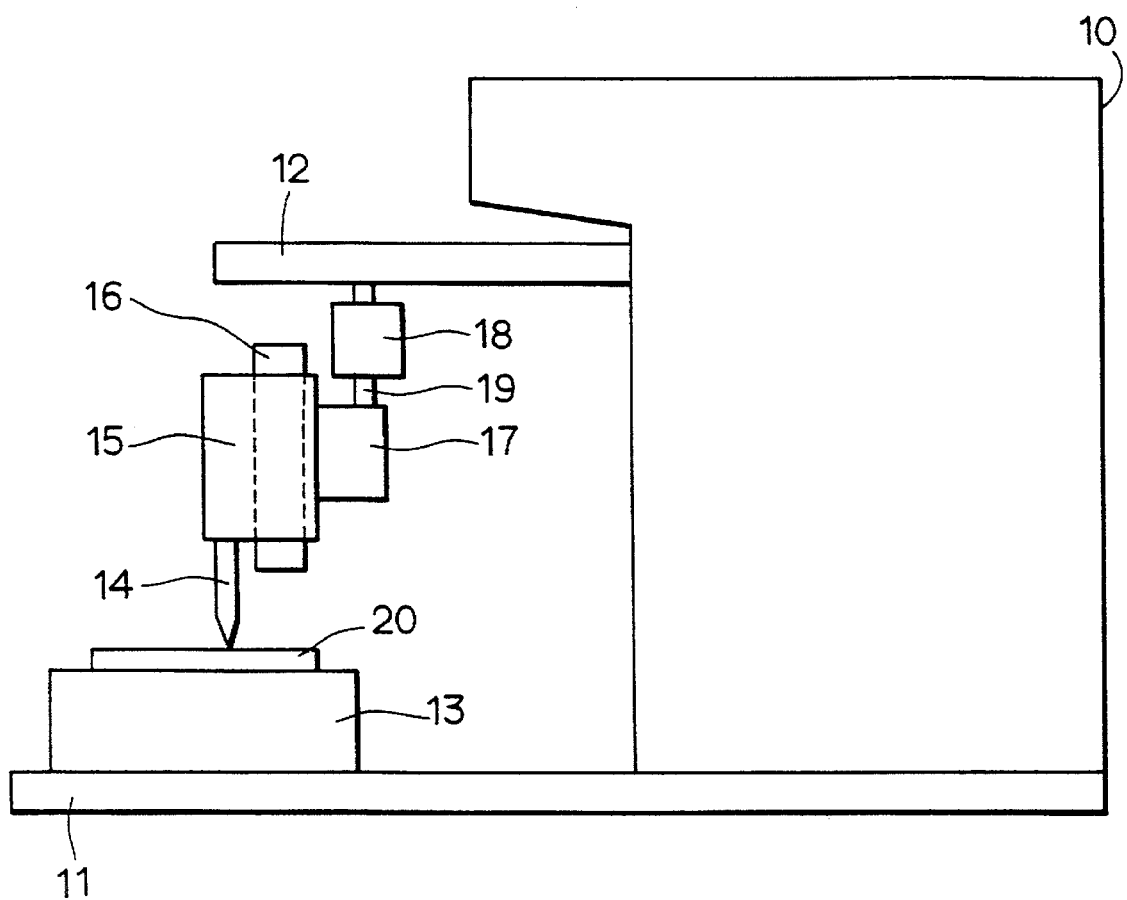
FIG. 1 is a schematic view showing an entire construction of a testing apparatus for semiconductor bump electrodes according to an embodiment of the present invention.

In FIG. 1 showing an entire structure of a semiconductor bump electrode testing apparatus according to an embodiment of the present invention, the testing apparatus has a main body 10, a base 11 fixed under the main body 10 and a movable part 12 provided at the upper portion of the main body 10. The movable body 12 is driven by a driving mechanism (not shown) installed in the main body 10 and moves up and down. A column 19 is fixed to the lower side of the movable part 12 vertically and supports a load cell 18 thereon. The load cell 18 may be a well-known converter for converting force (load) or weight to an electrical signal proportional to the force (load) or the weight. It outputs the electric signal to a detecting portion (not shown) arranged in the main body 10.

Under the load cell 18, a heat insulator 17 is arranged via the column 19. A jig 15 made of a metal is attached to the heat insulator 17. A heater 16 is mounted in the jig 15 and a probe 14 is attached to the bottom of the jig 15. The probe 14 and the heater 16 are coupled with each other so that the heat from the heater 16 is transferred to the probe 14, while the heat transfer to the load cell 18 is prevented by the heat insulator 17. A mounting table 13 is placed on the base 11 and a semiconductor chip 20 which is to be tested with respect to the bump electrode pull strength is mounted on the mounting table 13.

Figure 2:
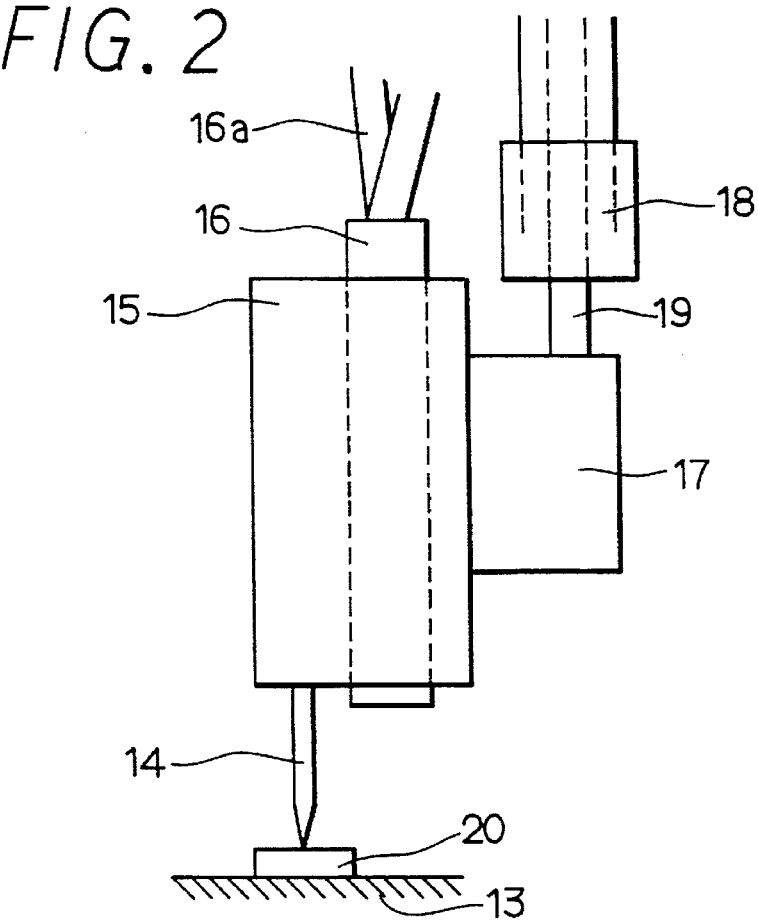
FIG. 2 is an enlarged view showing a tip portion and a heater portion of the testing apparatus for the semiconductor bump electrodes shown in FIG. 1.
Figure 3:
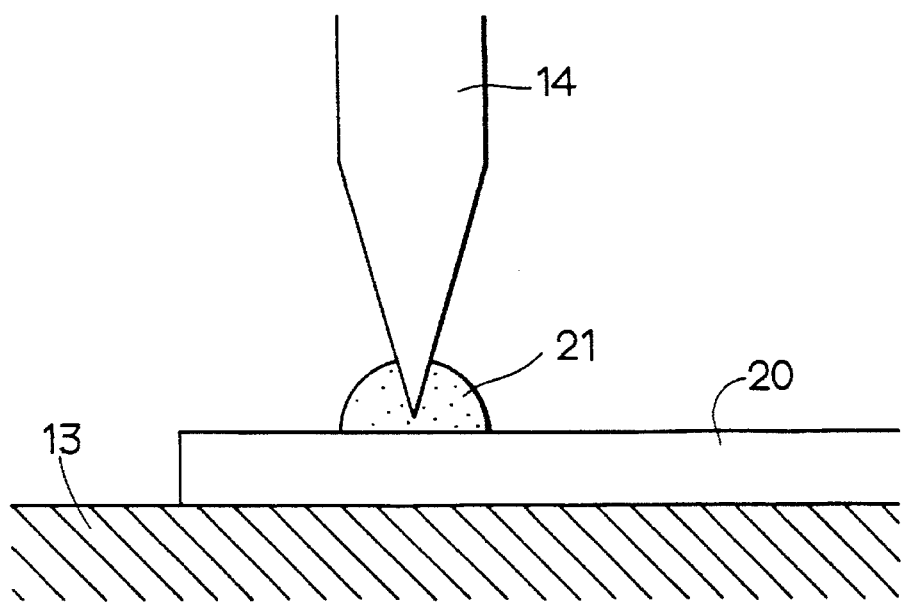
FIG. 3 is a still further enlarged view showing the tip portion of the testing apparatus for the semiconductor bump electrodes shown in FIG. 2.

As shown in FIGS. 2 and 3 showing the heater portion and the probe tip portion of the testing apparatus according to the present embodiment in an enlarged manner, the jig 15 is made of a good heat conductive metal such as brass and the heater 16 is supported therein. The heater 16 is supplied with the electric power from a power source (not shown) disposed in the main body 10 via power supply cables 16a.

The probe 14 is made of a metal having a good heat conductivity and good wettability with bump electrodes 21 and formed in a needle shape. Such metal may include copper, silver, platinum, copper alloy such as Zr-Cu, Fe-Cu, Ni-Cu or the like, or an iron alloy such as 42-alloy (42% Ni-Fe) or the like. The probe 14 formed in the needle shape is formed further, at the tip end thereof which contacts the bump electrodes 21, in a pointed, circular or flat shape.

Next, operation of the semiconductor bump electrode testing apparatus according to the present invention will be described.

First, the probe 14 made of copper is moved downward to stick or press the soldered bump electrode 21 (FIG. 3) formed on the semiconductor chip (or semiconductor wafer) 20. Next, while keeping the copper-made probe 14 stuck into or pressed onto the soldered bump electrode 21 (FIG. 3), the heater 16 heats up to the temperature at which the solder of the soldered bump electrode 21 is fused (about 250° C. in the case of using an eutectic solder) so that the solder of the soldered bump electrode 21 is fused. After the solder of the soldered bump electrode 21 has been fused by the heating of the heater, heating the heater 16 is stopped and then it is cooled down to the room temperature to solidify the fused solder again. At the time of solidifying the solder the copper-made probe 14 is fixedly held within the soldered bump electrode 21.

Figure 4A:
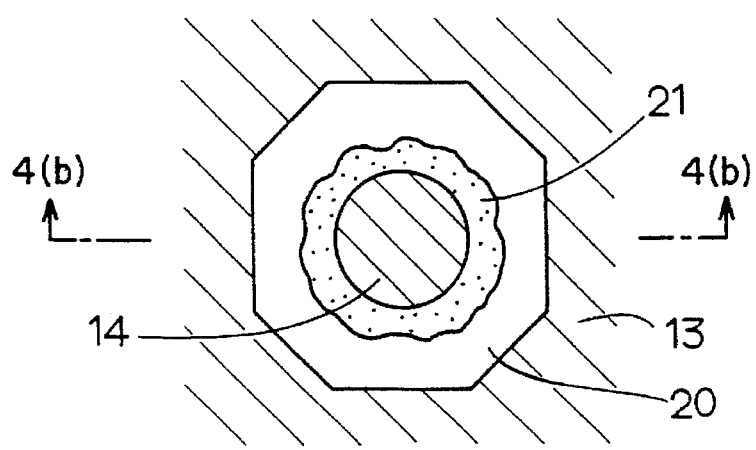
FIG. 4 is a schematic view showing breakage of the semiconductor bump electrodes which is caused by the testing apparatus for the semiconductor bump electrodes according to the embodiment of the present invention.
Figure 4B:
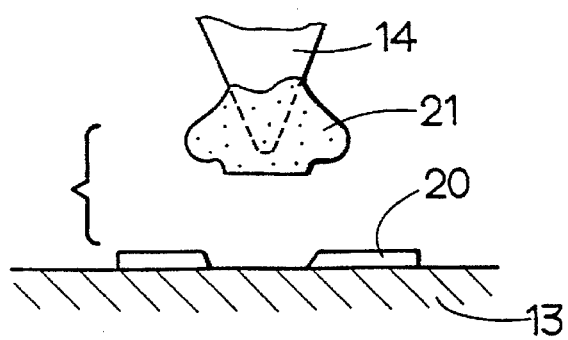
Figure 5:
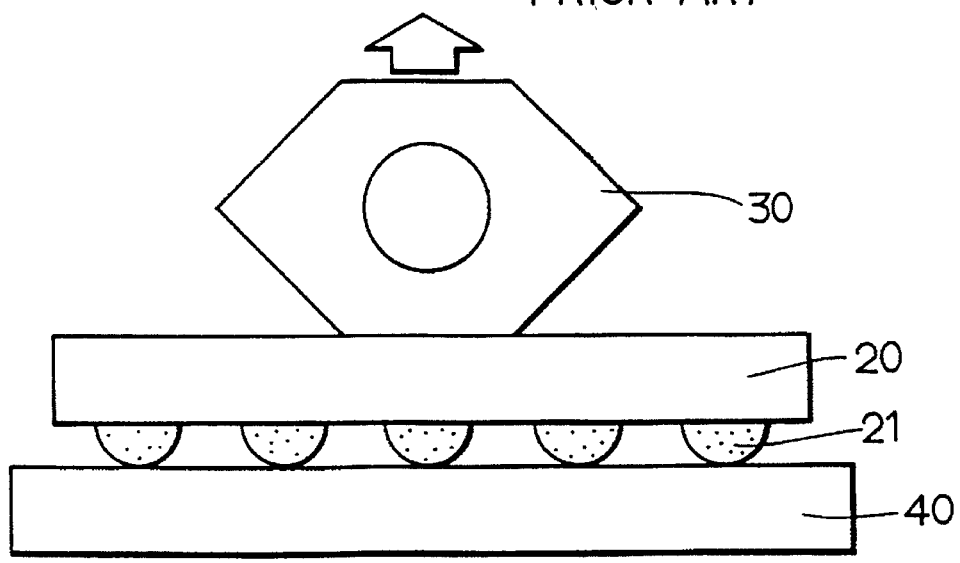
FIG. 5 is a schematic view showing an example of breaking the semiconductor bump electrodes by the use of a conventional testing apparatus for semiconductor bump electrodes.

The movable part 12 is moved upward by the driving mechanism (not shown) installed in the main body 10 of the testing apparatus for the semiconductor bump electrodes and pulls up vertically the copper-made probe 14 fixedly held within the soldered bump electrode 21. FIG. 4 shows in (a) and (b) thereof the bump electrode 21 broken away from the semiconductor chip 20 and fixed to the probe 14 after the pulling operation. The pulling strength is measured during this operation and, at the time of breakage of the soldered bump electrode 21 (FIG. 4), the measured value is output as the pull strength or the tensile strength of the bump electrode 21. The following table I shows the measurement values corresponding to the electric signal outputted from the load cell 18 at the time of the bump electrode breakage in the pull strength testing.

TABLE I

| Electrode Strength in Pull Testing | | | |
|---|---|---|---|
| Pulling Strength Result | 210 g/bump | Average Pull Strength | 177.6 g/bump |
| | 160 g/bump | | |
| | 170 g/bump | | |
| | 145 g/bump | Standard Deviation | 28.0 |
| | 203 g/bump | | |

According to the present embodiment constructed as above, the pull strength or tensile strength can be measured for each soldered bump electrode 21 without mounting the soldered bump electrodes 21 of the semiconductor chip (or semiconductor wafer) 20 onto an object such as the substrate. Further the adhesive, which will otherwise break when used at the tip of the probe 14 to connect the soldered bump electrode 21 and the probe 14, will never occur. Thus the pulling strength and the breakage mode can be measured accurately with respect to each of the soldered bump electrodes 21.

It is to be understood in the above embodiment that the stress force is exerted to the load cell 18 during the testing period until the electrode 21 breaks, because the probe 14 is fixed with the electrode 21 of the semiconductor chip 20 kept fixedly placed on the table 20 and the movable part 12 moves up. The load cell 18 converts this stress force into the corresponding electric signal by a strain gauge or the like mounted therein.

Furthermore, because the heat insulator 17 is interposed between the load cell 18 and the heater 16 to prevent the heat transfer of the heater 16 for heating the probe 14 to the load cell 18, The load cell 18 will not operate erroneously and accurate measurement can be performed. In addition, since the probe 14 uses such a metal as having a good wettability to the solder of the soldered bump electrodes 21, the fixing between the soldered bump electrodes 21 and the probe 14 can be assured most advantageously. In the above embodiment, the heater 16 may be supplied with the electric power first and then, after the temperture rises sufficiently high to fuse the soldered bump electrode 21, the probe may be moved down to contact the soldered bump electrode 21 to fuse the same.

The present invention having been described hereinabove may be modified in many other ways without departing from the spirit of the present invention.

I claim:

1. A method for testing a pull strength of a semiconductor bump electrode comprising the steps of:

heating a probe to be inserted into said semiconductor bump electrode to a temperature at which a metal of said bump electrode melts;

contacting said heated probe to said metal of said bump electrode to melt said metal of said bump electrode;

stopping heating of the probe once said bump electrode melts;

cooling down said melted metal of said bump electrode to solidify the same with said probe fixed in said solidified bump electrode;

after said bump electrode has solidified, pulling said probe fixed in said bump electrode; and measuring a pulling force at the time of the pulling operation to test the pull strength of said bump electrode.

2. A method of testing a pull strength of a semiconductor bump electrode comprising the steps of:

inserting a probe into said semiconductor bump electrode;

heating said probe to a temperature at which a metal of said semiconductor bump electrode is melted to melt said metal of said semiconductor bump electrode;

stopping heating of the probe once the bump electrode melts;

cooling down said metal of said bump electrode to solidify the same with said probe fixed in said solidified bump electrode;

after said bump electrode has solidified; pulling said probe fixed in said bump electrode; and measuring a pulling force at the time of the pulling operation to test said pull strength of said bump electrode.

3. A method for testing a semiconductor bump electrode according to claim 2, wherein said pulling step pulls said probe vertically relative to said bump electrode until said bump electrode is broken; and wherein said measuring step outputs a measured value of said pull force at the time of breakage of said bump electrode.

4. A method for testing a semiconductor bump electrode according to claim 3, wherein said pull force at the time of said breakage of said bump electrode is measured by converting the same into an electric signal by a load cell.

5. An apparatus for testing a semiconductor bump electrode, said apparatus comprising:

a probe constructed and arranged to contact said semiconductor bump electrode;

a heater heat-transferably coupled with said probe for heating said probe to a temperature which melts the bump electrode;

a pulling device for pulling said probe, said probe being constructed and arranged to heat said bump electrode so that said bump electrode is melted and fixed to said probe upon cooling thereof; and a load cell operatively connected to said probe and converting a pulling force of said pulling device to an electric signal corresponding to the pulling force.

6. An apparatus for testing a semiconductor bump electrode, said apparatus comprising:

a probe movable to said semiconductor bump electrode;

a heater for heating said probe to a temperature at which a metal of said bump electrode is melted;

a probe moving means for moving said probe up and down;

a jig holding said probe at a tip thereof; and a load cell mounted on said probe moving means for converting into an electric signal a pulling force of said probe from said semiconductor bump electrode when said probe is pulled by said probe moving means after said semiconductor bump electrode is melted and thereafter solidified with said probe fixed in said semiconductor bump electrode.

7. An apparatus for testing a semiconductor bump electrode according to claim 6, further comprising:

a heat insulator interposed between said heater and said load cell for preventing transfer of heat of said heater to said load cell.

8. An apparatus for testing a semiconductor bump electrode according to claim 7, wherein said probe is made of a metal having a good wettability with a metal of said bump electrode.

9. An apparatus for testing a semiconductor bump electrode according to claim 8, wherein said metal having said good wettability with said metal of said bump electrode is made of at least one of a metal or an alloy selected from copper, silver, platinum, iron alloy and copper alloy.

10. An apparatus for testing a semiconductor bump electrode according to claim 6, wherein said probe is made of a needle member having a tip formed in a pointed shape.

11. An apparatus for testing a semiconductor bump electrode according to claim 6, wherein said probe is made of a needle member having a tip formed in a round shape.

12. An apparatus for testing a semiconductor bump electrode according to claim 6, wherein said probe is made of a needle member having a tip formed in a flat shape.

13. A method for testing a semiconductor bump electrode according to claim 1, wherein said probe and said bump electrode are made of different materials.

14. A method for testing a semiconductor bump electrode according to claim 13, wherein a melting point of said probe is higher than a melting point of said bump electrode such that during said heating step, said bump electrode is melted without melting said probe.

15. A method for testing a semiconductor bump electrode according to claim 1, wherein said pulling step pulls said probe together with said bump electrode until said bump electrode is severed from a semiconductor chip; and said measuring step outputs a measured value of said pull force at the time of breakage of said bump electrode.

16. A method for testing a semiconductor bump electrode according to claim 2, wherein said probe and bump electrode are made of different materials.

17. A method for testing a semiconductor bump electrode according to claim 16, wherein a melting point of said probe is higher than a melting point of said bump electrode such that during said heating step, said bump electrode is melted without melting said probe.

18. A method for testing a semiconductor bump electrode according to claim 2, wherein said pulling step pulls said probe together with said bump electrode until said bump electrode is severed from a semiconductor chip; and said measuring step outputs a measured value of said pull force at the time of breakage of said bump electrode.

19. An apparatus for testing a semiconductor bump electrode according to claim 5, wherein said probe and said bump electrode are made of different materials such that during heating of said bump electrode, said bump electrode is melted without melting said probe.

20. An apparatus for testing a semiconductor bump electrode according to claim 6, wherein said probe and said bump electrode are made of different materials.

21. An apparatus for testing a semiconductor bump electrode according to claim 20, wherein a melting point of said probe is higher than a melting point of said bump electrode such that during heating of said bump electrode, said bump electrode is melted without melting said probe.

22. A method for testing a pull strength of a semiconductor bump electrode, comprising the steps of:

heating a metal of a bump electrode to be tested until said metal melts;

cooling down said melted metal of said bump electrode to solidify the same while keeping a metal probe in contact with said bump electrode;

causing relative movement between said metal probe and said metal of the bump electrode after said metal of said bump electrode has solidified; and measuring either a pull strength or a tensile strength of said metal of said bump electrode at a time of separation between said metal of said bump electrode and said metal probe.

23. A method for testing a pull strength of a semiconductor bump electrode, comprising the steps of:

heating a metal of a bump electrode to be tested until said metal melts;

providing a metal probe;

cooling down said melted metal of said bump electrode to solidify the same while fixing said metal probe in said bump electrode;

causing relative movement between said metal probe and said metal of the bump electrode after said metal of said bump electrode has solidified; and measuring either a pull strength or a tensile strength of said metal of said bump electrode at a time of separation between said metal of said bump electrode and said metal probe.

* * * * *